United States Patent [19]
Doiron et al.

[11] Patent Number: 5,687,730
[45] Date of Patent: Nov. 18, 1997

[54] APPARATUS FOR DETECTING THE PRESENCE OF ABNORMAL TISSUE WITHIN A TARGET TISSUE BENEATH THE SKIN OF A PATIENT

[75] Inventors: Daniel R. Doiron, Santa Ynez; A. Charles Lytle, Nipomo, both of Calif.

[73] Assignee: PDT Systems, Inc., Goleta, Calif.

[21] Appl. No.: 557,903

[22] Filed: Nov. 14, 1995

Related U.S. Application Data

[63] Continuation-in-part of Ser. No. 378,056, Jan. 25, 1995, abandoned, which is a continuation of Ser. No. 189,122, Jan. 27, 1994, abandoned, which is a continuation of Ser. No. 113,711, Aug. 26, 1993, abandoned, which is a continuation of Ser. No. 20,266, Feb. 18, 1993, abandoned, which is a continuation of Ser. No. 644,961, Jan. 22, 1991, abandoned.

[51] Int. Cl.$^6$ .................................................. A61B 5/00
[52] U.S. Cl. ........................................................ 128/665
[58] Field of Search ..................................... 128/633–634, 128/665, 666, 664; 607/88–90, 92, 93; 606/2, 3, 10, 13–16

[56] References Cited

U.S. PATENT DOCUMENTS

| | | | |
|---|---|---|---|
| 4,178,917 | 12/1979 | Shapiro | 128/665 |
| 4,718,417 | 1/1988 | Kittrell et al. | 128/634 |
| 4,752,115 | 6/1988 | Murray, Jr. et al. | 128/665 |
| 4,957,114 | 9/1990 | Zeng et al. | 128/665 |
| 5,003,977 | 4/1991 | Suzuki et al. | 128/633 |
| 5,062,431 | 11/1991 | Potter | 128/665 |
| 5,239,998 | 8/1993 | Krauthamer | 128/665 |

*Primary Examiner*—Ruth S. Smith
*Attorney, Agent, or Firm*—Michael G. Petit

[57] ABSTRACT

An apparatus for detecting the presence of cancerous tissue using fluorescence. The apparatus employs an external light source capable of delivering about 50 milliwatts of excitation power within the absorption spectrum of tumor-specific target fluorescent molecules. Excitation light enters the fluorescent probe where it is chopped and divided, a portion being transmitted through an optical fiber to endogenous or exogenous photosensitive molecules on the surface of the tumor. The photosensitive molecules, once excited, generate a fluorescence spectrum characteristic of the cell type. The fluorescence emitted from the excited photoactive molecules on the tumor enters the optical fiber and passes to the fluorescence probe where it is filtered and analyzed. The use of the single fiber for both excitation and detection of fluorescence light enables the probe to be inserted into extremely small openings. The fluorescence probe will measure the magnitude of excitation light delivered and reflected from the tissue thereby giving a quantitative measurement of the fiber tip-to-tissue distance and tissue optical characteristics. The apparatus also can distinguish variations in fluorescence due to differences in distance of the fiber tip from the tissue under investigation by measuring the ratio of fluorescence and/or reflectance at two different wavelengths.

1 Claim, 2 Drawing Sheets

APPARATUS FOR DETECTING THE PRESENCE OF ABNORMAL TISSUE WITHIN A TARGET TISSUE BENEATH THE SKIN OF A PATIENT

This application is a continuation-in-part of U.S. Ser. No. 08/378,056 filed Jan. 25, 1995, now abandoned, which is a continuation of U.S. Ser. No. 08/189,122 filed Jan. 27, 1994, now abandoned, which is continuation of U.S. Ser. No. 08/113,711 filed Aug. 26, 1993, now abandoned, which is continuation of U.S. Ser. No. 08/020,266 filed Feb. 18, 1993, now abandoned, which is continuation of U.S. Ser. No. 07/644,961 filed Jan. 22, 1991, now abandoned.

BACKGROUND OF THE INVENTION

1. Field of the Invention

The present invention relates to a method and apparatus for detecting the presence of cancerous tissue and, more particularly, to a method and apparatus for detecting cancerous tissue using fluorescence.

2. Prior Art

This invention is based on the discover that the visible fluorescence spectrum for cancerous and non-cancerous tissue are substantially different and that the differences are such that fluorescence from tissue can be used to detect the presence of cancer. Certain biological molecules fluoresce differently in cancerous and non-cancerous tissue. In general, the fluorescence spectrum is shifted to lower wavelengths in tissues possibly corresponding to high concentration of flavin and porphyrin peaks.

Porphyrin fluorescence is enhanced in cancerous tissue. The porphyrin molecules are most likely in disassociated state as this is the only form that fluoresces. The abundance of free porphyrins in cancerous tissue may result from a reduction of the metal ion that serves to build the porphyrins in the proteins. Zeng et al, in U.S. Pat. No. 4,957,114 (issued Sep. 18, 1990), incorporated herein by reference, describes an apparatus for the fluorescence detection of cancerous tissue using a near ultraviolet light source with a wavelength of 3,000–4,000 A. The energy of the stimulating beam is close to the absorption peak (3400 A, +/−200 A) exhibited by a malignant tumor. The Zeng et al apparatus embodies soft, flexible fiber optic cables to transmit stimulating light from the light source to the surface of the tumor tissue and to transmit the intrinsic fluorescence from the tumor to a color resolution system. The apparatus may be used to diagnose malignancy on a body surface or within a body cavity. The Zeng apparatus uses a separate fiber for the delivery of excitation light and fluorescence detection.

Alfano et al, in U.S. Pat. No. 4,930,516 (issued Jun. 5, 1990), incorporated herein by reference, describes an apparatus for detecting the presence of cancerous tissue using visible luminescence. In the Alfano apparatus, the tissue to be examined is excited with a beam of monochromatic light causing the tissue to fluoresce over a spectrum of wavelengths. The intensity at which the excited tissue fluoresces can be measured either over a spectrum or at a predetermined number of pre-selected wavelengths. By determining the wavelengths at which maximum intensities are obtained for the tissue in question and by comparing these peak values either visually or electronically to the peak wavelengths derived from a known non-cancerous tissue or by comparing the spectrum of the excited tissue with the spectrum of a known non-cancerous tissue, one can distinguish between normal and cancerous tissue. The Alfanos teach the use of photomultiplier tubes for detection of luminescence and the advantages of a lock-in amplifier for phase-sensitive detection.

The apparatus described in the Alfano et al patent has several disadvantages. The use of photomultiplier tubes for fluorescence detection is not recommended inasmuch as photomultiplier tubes are easily destroyed by ambient light. In addition, separate fiber bundles are used for carrying excitation and fluorescence light. While there is only one fiberoptic "probe" shown in the Alfano et al apparatus actually four fibers are required, one to deliver the excitation light and three to pick up the fluorescence light and channel it to separate detectors.

The use of multiple optical waveguides creates a number of problems. Endoscopic procedures with two or more fibers require the use Of larger, more cumbersome dual channel endoscopes. This limits the efficacy of some procedures such as bronchoscopies which can examine much further into the bronchial tree with the small, more flexible single channel scopes. It is also very difficult to accurately orient the tips of the plurality of fibers relative to each other. Separation between two or more fibers creates, at close distance to the measured tissue, non-overlapping fields of view between the excitation source and the fluorescence pickup, see, for example, FIG. 3. It is, therefore, desirable to provide a fluorescence probe capable of distinguishing between cancerous and non-cancerous tissue having a single fiber which is used to both deliver the excitation light and to pick up the fluorescence.

The fluorescence probe of the current invention is a real-time clinical diagnostic device which overcomes the foregoing problems with prior art devices and can help the physician identify the margins of cancerous lesions in-situ. The probe is also useful in Photodynamic Therapy (PDT) to quantify photosensitizer concentrations in vivo and as an aid in therapeutic dosimetry.

SUMMARY OF THE INVENTION

An object of the current invention is to provide a fluorescent probe utilizing a single optical waveguide (optical fiber) for transmission of both excitation and fluorescence light. The present invention overcomes the problems of the prior art resulting from the use of multiple fibers by using a single fiber. The excitation light is delivered to the laser input port of the fluorescence probe and the internal optics within the fluorescence probe couples the light back to a single delivery fiber port. The fluorescence probe's input optics separate the returning fluorescence by color and focuses the light on photodiode detectors.

Another object of the invention is to provide a fluorescence probe which may be used during simultaneous white light examinations while preventing damage to the detectors.

It is yet a further object of this invention to provide a fluorescence probe to accurately measure fluorescence levels regardless of the patient-to-patient differences in cellular composition or marker drug concentration.

It is still a further object of this invention to provide a fluorescence probe with means for correcting for errors due to the fourth power decay of the fluorescence as the distance between the tissue and the fiber tip increases.

It is yet a further object of this invention to provide a fluorescence probe for the detection of cancerous tissue which may be used with an independent excitation source. A white light source or a laser may be used if enough in band power can be coupled to the delivery fiber.

It is another object of this invention to provide a fluorescence probe which will measure the magnitude of the excitation light that is reflected from the tissue thereby giving a quantitative measure of the fiber tip-to-tissue distance, an indication of fiber tip contamination, and is useful in quantifying pigmentation levels in the tissue.

It is yet another object of this invention to provide a fluorescence probe which permits internal chopping of an external light source and accurate phase matching of the fluorescence signal with the excitation signal for greater sensitivity.

The realization of these and other objects of the invention can be more clearly understood by turning now to the drawings.

DESCRIPTION OF THE PREFERRED EMBODIMENT

Figure 1:
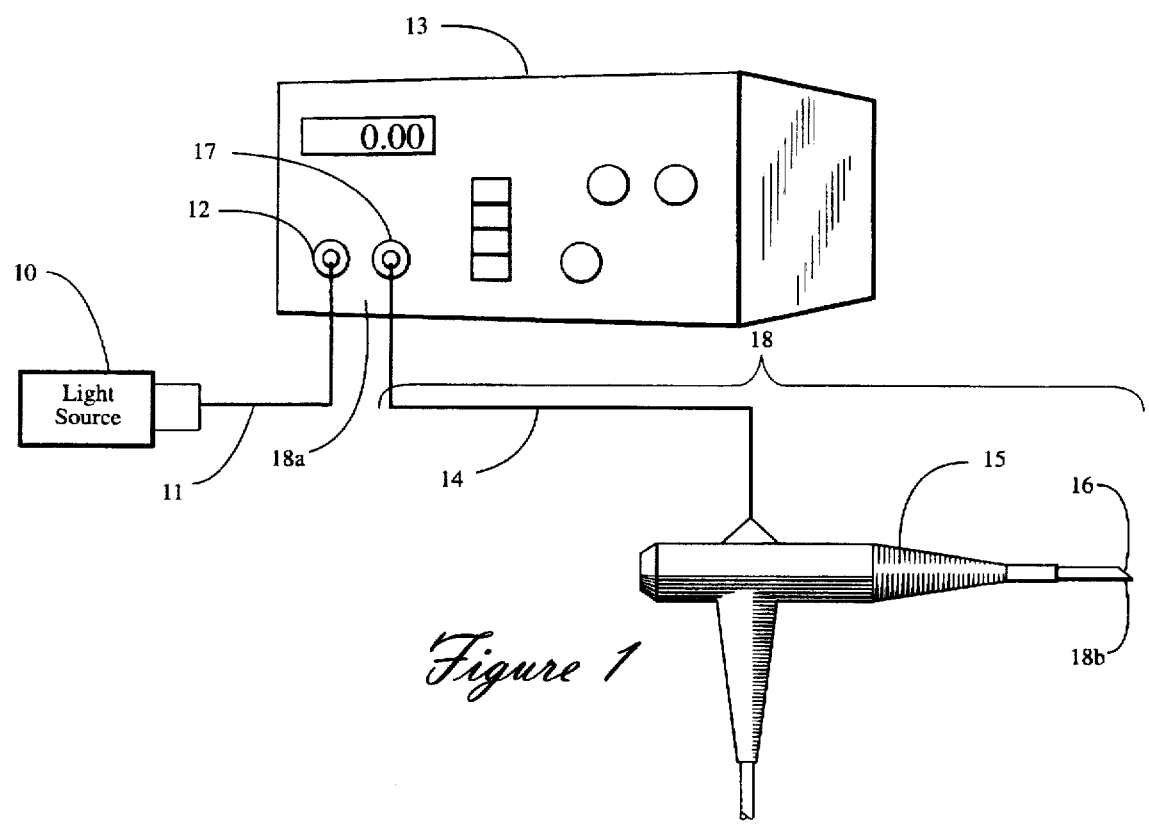
FIG. 1 is a schematic diagram of a general endoscopic system employing the fluorescence probe of the current invention.

Turning first to FIG. 1, in a preferred embodiment from a laser 10 having a wavelength within the absorption spectrum of photosensitive tumor specific molecules, is transmitted via fiberoptic 11 to the input port 12 of the fluorescence probe 13. The laser light (excitation beam) enters the internal optics of the fluorescence probe 13 which chops and passes a portion of the excitation beam to output port 17 (and sometimes hereinafter referred to as input/output port 17). The excitation light exits the fluorescence probe through output port 17 then passes through detection fiber 14 to an endoscope 15. The excitation light passes through an optic fiber (not shown) within the endoscope and out the tip 16 to impinge upon target tissue. The detection fiber 14 and optical fiber in the endoscope are sometimes hereinafter referred to as a fiber optic waveguide 18, having a proximal end 18a and a distal end 18b. Luminescence (both fluorescence and reflected light) from the target tissue enters the tip 16 of the endoscope 15 and is transmitted back through the detection fiber 14 to the output port 17 where a portion is passed on to a synchronous detector.

Figure 2:
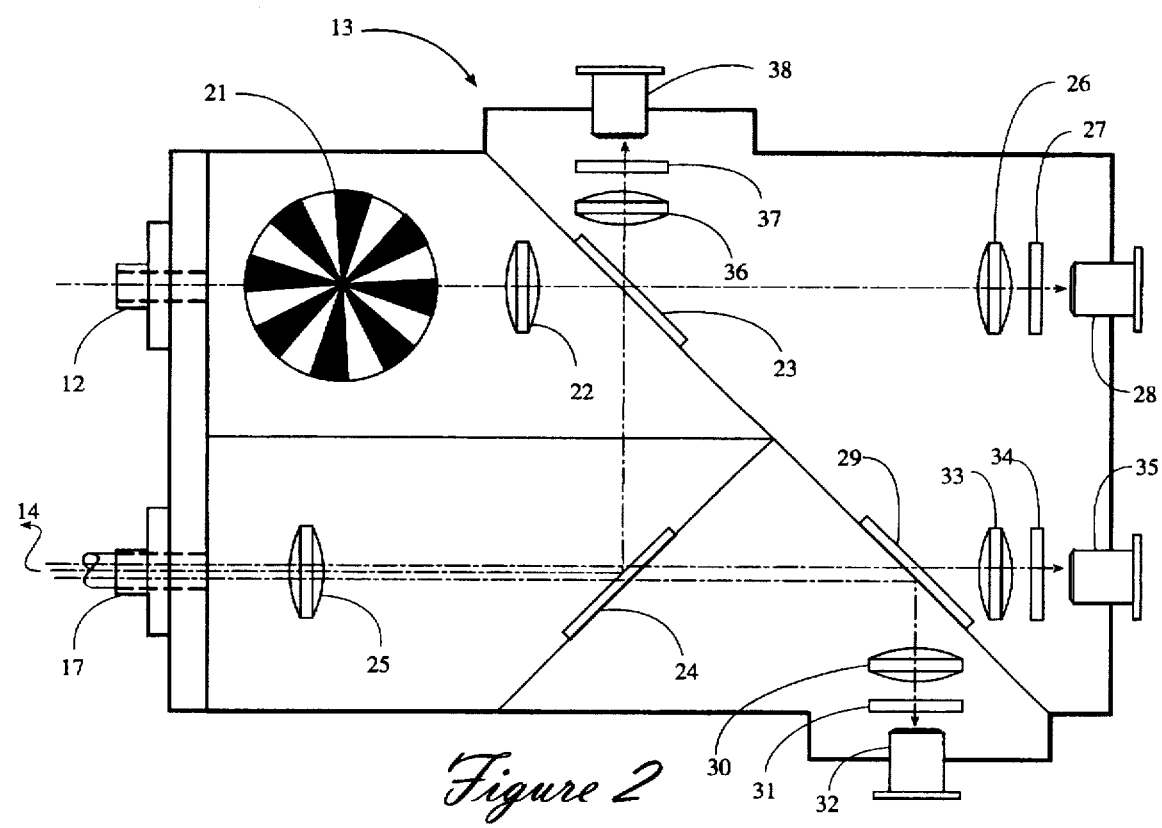
FIG. 2 is a schematic diagram of a preferred embodiment of the optical components of the fluorescence probe of the current invention.

Referring now to FIG. 2, the internal optics of a preferred embodiment of the fluorescence probe 13 of the current invention is shown. The UV or blue light from a excitation source 11 enters the fluorescence probe 13 through input port 12. If the excitation source is continuous, it passes through a microwheel chopper 21 and is brought to focus on a dichroic mirror 23 by means of an input collimating lens 22. The input or excitation light is divided at the dichroic mirror 23, a major portion of it passing to a second dichroic mirror 24. Dichroic mirror 24 reflects the UV-blue excitation light while passing longer wavelengths. The reflected portion of the excitation light is brought to focus on the output fiberoptic port 17 by means of output lens 25 where it exits the fluorescence probe 13 via the detection fiber 14 (FIG. 1) which conducts the excitation light to the target tissue (not shown) near the tip 16 of the endoscope 15. The fluorescence light emitted by the target tissue passes up the detection fiber 14 (FIG. 1) and re-enters the fluorescence probe via port 17 where the output lens 25 brings it once again to focus on the second dichroic mirror 24. The longer wavelength portion of the fluorescence signal is passed through the dichroic mirror 24 to impinge upon a third dichroic mirror 29 which separates the longer wavelength and passes the corresponding light through to the appropriate detector 35 by means of a lens 33 and a filter 34. The other wavelength of light is then reflected to the appropriate detector 32 by means of lens 30 and filter 31.

As previously mentioned, the original excitation beam entering the fluorescence probe through port 12 is chopped by means of a microwheel chopper at a frequency of about 500 pulses per second then is split at dichroic mirror 23. A transmitted portion of the excitation beam passes to the synchronization detector 28 by means of lens 26 and filter 27. The synchronization detector 28 sets the lock-in frequency of the detector and serves as a reference. The red component of the fluorescence light is then detected by the red light detector 35 and the fluorescence intensity measured.

Light from the excitation beam by the target tissue also enters the fluorescence probe via output port 17, passing through the output lens 25 to the second dichroic mirror 24 where it is reflected to pass through the first dichroic mirror 23 onto the reflectivity detector 38 by means of lenses 36 and filter 37. The intensity of the reflected light, when compared to the intensity of the excitation light and intrinsic fluorescence of the tissue, can give a quantitative measurement of the fiber tip to tissue distance, an indication of fiber contamination, and is useful in quantifying pigmentation levels in the tissue.

By using amplified photodiodes to detect the fluorescent light, there is no possibility of ambient light doing damage to the detectors. Photomultiplier tubes, used in some prior art fluorescence detection devices are very easily damaged by exposure to room light. This allow the fluorescence probe of the current invention to be used during simultaneous white light examination.

The electronics in the probe are designed to extract the induced fluorescent signal from the much stronger background light. In applications using a 50% chopped CW excitation source, lock-in amplifiers extract the amplitude of only that light which is in phase with the excitation source. This eliminates any in band background light leaking to the detector(s) from room lights or the white endoscopic light source. If pulsed laser excitation is used, the chopper 21 is not used and the fluorescence signal is sampled at the peak of the excitation pulse and again during the dark interval between laser impulses. Subtracting these values will again cancel out the background light. The combination of using photodiodes and the sampling electronics allow the fluorescence probe to function in room light or under the white light illumination of an endoscopic procedure.

A light chopper 21 built into the fluorescence probe eliminates the problems in synchronizing the lock-in amplifier to an external chopper. The synchronizing signal is generated internally in the probe by detecting the chopped excitation light with a dedicated photodiode (not shown). This eliminates the need for the difficult alignment procedure required by units using a separate external chopping system.

Figure 3A:
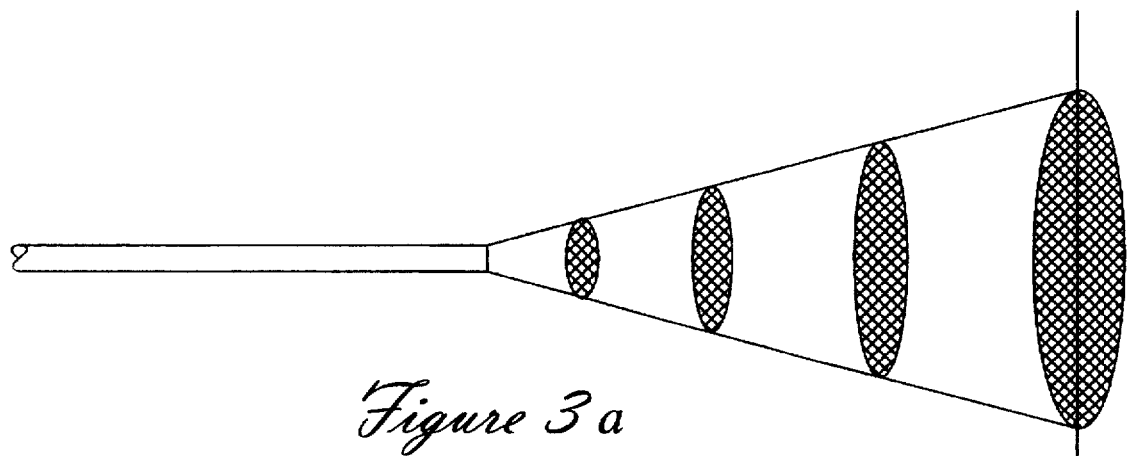
FIG. 3 compares the overlap of fields using a single fiber for carrying both excitation and fluorescent light (FIG. 3(a)) and using separate fibers (FIG. 3(b)).
Figure 3B:
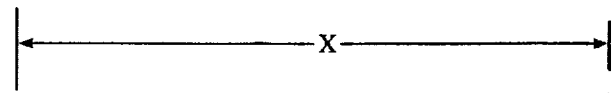
Figure 3B:
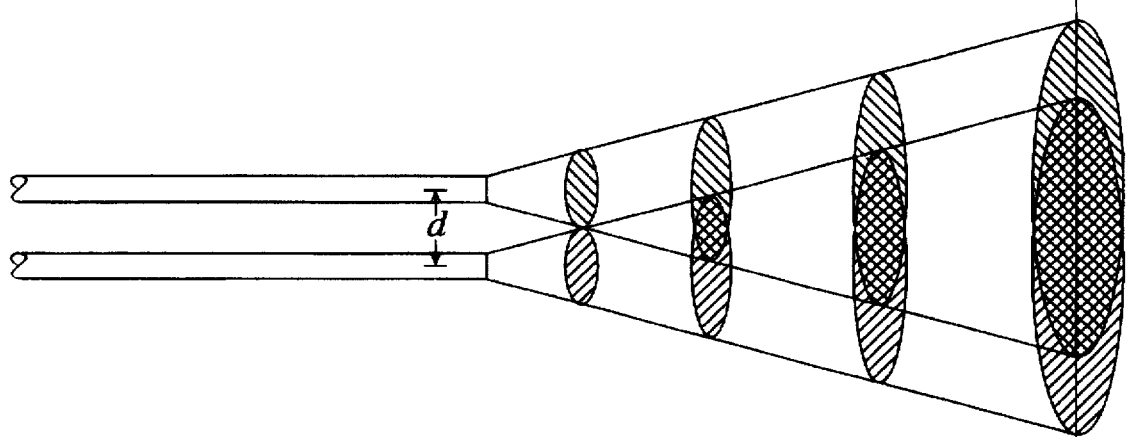

In other fluorescence detection systems, two or more fibers are required, one to deliver the excitation light and one or more to pick up the fluorescence light. This creates a number of problems. Endoscopic procedures with two fibers require the use of larger, more cumbersome dual channel endoscopes. This limits the efficacy of some procedures such as bronchoscopies which can examine much farther into the bronchial tree with the small, more flexible single channel scopes. It is also very difficult to accurately orient the tips of two or more optical fibers relative to each other. As shown in FIG. 3b, the separation d between the two fibers creates, at close distances (x) to the measured tissue, non-overlapping fields of view between the excitation source and the fluorescence pickup.

With the fluorescence probe of the present invention, a single fiber (FIG. 3a) is used to both deliver the excitation light and to pick up the fluorescence. Since the fields of view are identical, the fluorescence is detected even at very short distances. The excitation light is delivered to the fluorescence probe's input port 12 and the internal optics fold the light back to the single delivery fiber port 17. The optics comprising lens 25 and dichroic mirror 24 separate the returning fluorescence (at 630 nm and 570 nm) and focuses the light on the photodiode detectors. By using a fiber with very low in-band fluorescence and including a fiber calibration function, the fluorescence probe can subtract off the fiber fluorescence induced by the excitation light (intrinsic fluorescence), leaving only the desired target fluorescence. Due to the continuous monitoring of the delivered excitation power by detector 28, recalibration may be performed during a procedure, to compensate for variations in delivered power, and to correct for variations which may be introduced if the fiber is changed.

Because of the wide dynamic range in fluorescence levels which the probe must detect, auto ranging is a necessary feature. Electronics contained in the fluorescence probe (not shown) automatically ranges through three orders of fluorescence magnitude or may be locked in any range within the range-lock switch. This allows the probe to accurately measure fluorescence levels regardless of the patient or marker drug concentration. This is necessary due to the large variation in the fluorescence and reflectance signal magnitude with distance ($1/x^4$).

Measurement of fluorescence levels during a diagnostic procedure may be very difficult to interpret due to the fourth power decay of the fluorescence as the distance between the tissue and the fiber tip increases. To correct for this distance effect, the fluorescence level at 690 nm is divided by the level at 570 nm. This effectively minimizes the signal variations due to distance in the resulting ratio. Use of this ratio significantly adds to the detectability of the suspect tissue, and the comparison of the two wavelengths can also help to distinguish cancer by detecting differences in spectral shape. Variations in absolute fluorescence level from patient to patient, and tissue to tissue differences due to pigmentation variations are also reduced by using the ratio. An increase in the ratio by a factor of 3 or more would give a strong positive indication of cancerous tissue, over a 2 centimeter range in distance between the tissue and the fiber tip. A provision is also included for ratio to a control site. This allows for normalization of the ratio so that a reading of 1.00 corresponds to the ratio expected from normal tissue. Suspected areas could then within read 3.00 or more making it easier to identify potential tumor sites.

The fluorescence probe may be used with any light source capable of delivering 50 mw or more of excitation light in the photosensitizer absorption band to the probe. The source need not be a laser. A white light source may be used if enough in-band power can be coupled into the delivery fiber with rejection of the out-of-band power.

The fluorescence probe described above will also measure the magnitude of the excitation light that is reflected from the tissue. This can give a quantitative measurement of the fiber tip to tip tissue distance, an indication of fiber tip contamination, and is useful in quantifying pigmentation levels in the tissue.

The foregoing preferred embodiment has been given by means of example only and should not be limiting. Other modifications and variations of the invention may be made within the scope of the invention and in teachings, all as defined by the scope of the appended claims.

What we claim is:

1. An apparatus for detecting the presence of abnormal tissue within a target tissue beneath the skin of a patient comprising:

(a) a light source producing excitation light having a first wavelength;

(b) a fluorescence probe having an excitation light input port operable for receiving said excitation light from said light source, and an output/input port in optical communication with said excitation light input port;

(c) a fiber optic waveguide having a proximal end in optical communication with said output/input port of said fluorescence probe and a distal end, said fiber optic waveguide being operable for conducting said excitation light from said output/input port of said fluorescence probe to said distal end of said fiber optic waveguide, said fiber optic waveguide emitting fiber-derived intrinsic fluorescence light having a second wavelength when said excitation light is conducted therethrough, said excitation light thereafter to emerge from said distal end of said fiber optic waveguide to illuminate the target tissue causing the target tissue to emit target-derived light having said second wavelength and a third wavelength and wherein said fiber optic waveguide conducts combined fluorescence light comprising a portion of said target-derived light having said second and third wavelengths and a portion of said intrinsic fluorescence light having a second wavelength to said output/input port of said fluorescence probe;

(d) light dispersion means in optical communication with said output/input port operable for separating said combined fluorescence light into a portion of said combined fluorescence light having said second wavelength and a portion of said combined fluorescence light having said third wavelength;

(e) calibration means operable for subtracting off fiber fluorescence induced by said excitation light in said fiber optic waveguide from fluorescence measured, the difference being said portion of target-derived light at said second wavelength;

(f) means for converting said portion of target-derived light having said second wavelength to a first electronic signal having a signal strength related to the intensity of said portion of target-derived light having said second wavelength;

(g) means for converting said portion of targat-derived light having said third wavelength to a second electronic signal having a signal strength related to the intensity of said light having said third wavelength; and (h) means for measuring the ratio of said strength of said first electronic signal to said signal strength of said second electronic signal wherein a change in said ratio indicates a change in the amount of abnormal tissue within the target tissue.

* * * * *